United States Patent
Heismann

(10) Patent No.: US 7,889,834 B2
(45) Date of Patent: Feb. 15, 2011

(54) METHOD FOR PREPARING RECONSTRUCTED CT IMAGE DATA RECORDS AND CT SYSTEM

(75) Inventor: Björn Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 31 days.

(21) Appl. No.: 12/385,498

(22) Filed: Apr. 9, 2009

(65) Prior Publication Data

US 2009/0257549 A1 Oct. 15, 2009

(30) Foreign Application Priority Data

Apr. 10, 2008 (DE) .................. 10 2008 018 248

(51) Int. Cl.
*A61B 6/00* (2006.01)
(52) U.S. Cl. .................. 378/4; 378/5; 378/9
(58) Field of Classification Search .......... 378/4, 378/5, 98.11, 207
See application file for complete search history.

(56) References Cited

U.S. PATENT DOCUMENTS

| | | | |
|---|---|---|---|
| 4,686,695 | A * | 8/1987 | Macovski .......... 378/146 |
| 7,050,530 | B2 | 5/2006 | Heismann |
| 7,158,611 | B2 | 1/2007 | Heismann |
| 7,298,812 | B2 | 11/2007 | Bendahan et al. |
| 7,477,765 | B2 | 1/2009 | Heismann |
| 2002/0015476 | A1 * | 2/2002 | Reinwand et al. ........ 378/901 |
| 2005/0100125 | A1 * | 5/2005 | Heismann ................ 378/5 |
| 2006/0109949 | A1 * | 5/2006 | Tkaczyk et al. ........... 378/4 |
| 2006/0280281 | A1 * | 12/2006 | Flohr et al. .............. 378/5 |

FOREIGN PATENT DOCUMENTS

DE 10143131 B4 3/2006

OTHER PUBLICATIONS

B. Heismann et al.; Density and Atomic Number Measurements with Spectral X-Ray Attenution Method; J. of Appl. Phys., vol. 94 No. 3, 2003, 2073-2079; Others; 2003.
G.J. Michael: "Tissue analysis using dual energy CT" in "Australasian Physical & Engineering Sciences in Medicine, 1992, vol. 15, No. 1"; Magazine; 1992.
Robert E. Alvarez and Albert Macovski; Others; 1976; US, Energy-selective reconstruction in x-ray computerized tomography.

* cited by examiner

*Primary Examiner*—Edward J Glick
*Assistant Examiner*—Alexander H Taningco
(74) *Attorney, Agent, or Firm*—Harness, Dickey & Pierce, P.L.C.

(57) ABSTRACT

A method and CT system are disclosed for preparing reconstructed CT image data records. In at least one embodiment of the method, an initial material distribution of an examination object is determined from CT data records determined from among at least two different spectral weightings with local energy-determined attenuation values, and local measurement-spectrum-dependent weighting functions are determined using this material distribution, enabling local measurement-spectrum-dependent attenuation functions to be calculated, and the distribution of local reference materials to be determined, with the help of plausibility considerations, from a list of reference materials over at least one specified region of interest in the examination object on the basis of previously calculated local measurement-spectrum-dependent attenuation functions.

27 Claims, 9 Drawing Sheets

METHOD FOR PREPARING RECONSTRUCTED CT IMAGE DATA RECORDS AND CT SYSTEM

PRIORITY STATEMENT

The present application hereby claims priority under 35 U.S.C. §119 on German patent application number DE 10 2008 018 248.6 filed Apr. 10, 2008, the entire contents of which is hereby incorporated herein by reference.

FIELD

At least one embodiment of the invention generally relates to a method for preparing reconstructed CT image data records from N>2 projection data records, recorded with N different spectral weightings. An at least one embodiment relates to method including:
  CT scanning of an examination object and generation of the N projection data records each with different spectral weightings,
  reconstruction of N CT image data records, each with a large number of local image values, which reflect the local mean attenuation values at the location of the examination object and of a measurement field depending on the respective energy-dependent spectral weighting used for the scan.

According to at least one embodiment of the invention, the term spectral weighting means the product function $S_j(E)*D_j(E)$ in which j=1 to N, which—in energy-specific terms—is the product of the energy-dependent weighting of the radiation spectrum $S_j(E)$ used and the spectral sensitivity of a detector $D_j(E)$ that is used. The index j here stands for a different spectral weighting in each case. It is thus possible, by using different spectra and detectors with the same spectral sensitivity, or by using the same radiation spectra but with varying spectral detector sensitivities or even by simultaneously altering the spectral sensitivity of the detector and using different radiation spectra, to obtain spectrally differently weighted attenuation values in each case.

BACKGROUND

A general method and also CT systems for executing the procedure, are generally known. For example, it is possible—with the help of so-called dual-energy CT systems using two different X-ray radiation spectra—to reconstruct two tomographical image data records of the same examination object, which reflect the respective local attenuation values, or—more precisely—the local attenuation coefficients, that are influenced by the respective radiation spectrum used and by the spectral sensitivity of the detector used.

The measurement data is analyzed mainly by way of basic material decomposition, as described—for example—in PHYS. MED. BIOL., 1976, VOL. 21, NO. 5, 733-744, "Energy-selective Reconstructions in X-ray Computerized Tomography", R. E. Alvarez and A. Macovski, the entire contents of which are hereby incorporated herein by reference. In this method, two image data records showing the concentrations of basic materials are generated. Iodine and water or bone and water, for example, are used as typical basic materials. According to existing knowledge, a Rhoz projection may also be carried out on the basis of such tomographical image data records, as described in the publication DE 101 43 131 B4 (the entire contents of which are hereby incorporated herein by reference) or in the Journal of Applied Physics, "Density and atomic number measurements with spectral X-ray attenuation method", B. J. Heismann et al (the entire contents of which are hereby incorporated herein by reference). In this method the local density and atomic number are calculated on the basis of the energy-specific attenuation values that have been reconstructed via the tomographical image data records.

Such spectral methods achieve a material characterization through the calculation of indirect variables, such as the concentration of basic materials or the effective density and atomic number. Thus, for example, water may ordinarily be identified through a basic material composition of 1 part water and 0 parts bone or by an effective density of 1 g/cm³ and an effective atomic number of 7.5.

One alternative is direct identification of body materials. The measured-radiation-independent attenuation function of water $\mu_{water}(E)$ can be calculated with a high degree of accuracy. This is also possible for all organic and inorganic materials with known modular mass composition. In the *ICRU 46 Report*, for example, these attenuation functions are recorded for many body materials.

For direct identification of materials in CT on the basis of the image or attenuation values calculated therein, a number of limiting factors now emerge:
  Quantum noise forms a natural static limit for CT. An absorber may accordingly be identified only with a degree of probability, but not, however, with complete certainty. The dose required—at least in the field of medical applications
  must be carefully controlled. In positive terms the x-ray doses currently used in the medical field are sufficient for measuring weighted, so-called mean attenuation coefficients $\bar{\mu}_j(\vec{r})$, across the energy spectrum used, locally at the location $\vec{r}$ with an accuracy of approx. 0.3% to 1%. This corresponds to CT values of 3 to 10 HU per 1000 HU. This is, per se, a good statistical basis for using x-ray attenuation data for material identification.
  When an object is penetrated by an x-ray the latter is attenuated both by the photo effect and by the Compton effect. The Compton effect causes radiation scatter. The scattered x-ray quanta leave the attenuation path described by tubes and detector pixels. They are potentially measured in different detector channels as an error signal. By using collimators over the detector pixels, this signal proportion is greatly reduced—typically from several tens of percentage points to a few percent.
  In generally known methods, beam hardening leads to a local underestimation of attenuation values. The displacements that occur limit the accuracy of quantitative evaluations.

The identification of materials in an examination object is already being trialed on an image basis in several applications. Examples of this are the representation of uric acid (gout) or cardiac muscle damage. The limits described above with regard to dose, radiation scatter and beam hardening also apply in these cases.

A range of reconstructive correction processes also exists for reducing the effects of radiation scatter as a limiting factor in direct material identification, and these are used—in particular—in dual-source CT, since it is here that the effect of radiation scatter is relatively strong.

The so-called poly-correction process has hitherto been used mainly for correcting beam hardening. The purpose of such beam hardening correction methods is, in particular, to improve the display of the soft tissue gray level. Typical cupping effects or dark regions in the vicinity of bone are largely avoided with these known methods.

SUMMARY

In at least one embodiment of the invention, a method is disclosed for preparing reconstructed CT image data records in which the image data records are not affected by beam hardening or by measures to correct it, and in which any subsequent material allocation remains unaffected by spectral influences.

The inventor has noticed that beam hardening, in its effect on the reconstructed image values of tomographical image data records, whose pixels or voxels represent attenuation coefficients of the examined object or at least reflect them indirectly in the form of CT figures, is dependent upon the spectrum used by the scanning radiation and/or also upon on the spectral sensitivity of the detector used. It is, however, possible to describe the local mean attenuation values $\bar{\mu}_j(\vec{r})$ constructed with a CT as a function of a local spectral weighting function $\Omega_j(E,\vec{r})$ and of a non-measurement-spectrum-dependent—i.e. a local energy-dependent—attenuation function $\mu(E,\vec{r})$, and, on the basis of these local energy-dependent attenuation functions $\mu(E,\vec{r})$, to implement an improved material allocation, wherein the effects of any beam hardening are automatically avoided.

The problem of beam hardening can thus be described by means of a slowly varying, error-tolerant function that is also quick and easy to calculate. There is therefore a direct and clear relationship between the conventionally reconstructed local mean attenuation values $\bar{u}_j(\vec{r})$ and the local energy-dependent and thus measurement-spectrum-independent attenuation values $\mu(E,\vec{r})$ to be characterized by the spectral methods, according to the following equation:

$$\bar{\mu}_j(\vec{r}) = \int_E \Omega_j(E, \vec{r}) \mu(E, \vec{r}).$$

According to an embodiment of the invention, these local energy-dependent attenuation functions $\mu(E,\vec{r})$ may now be used in order to carry out a material decomposition, in which there are no disruptive influences resulting from potential beam hardenings.

Briefly, such a method may go as follows:

1. Measure and reconstruct at least two image data records of an examination object, consisting of local mean measurement-spectrum-dependent attenuation values $\bar{u}(\vec{r})$, in which j represents different spectral weightings, e.g. the 80 kVp and 140 kVp measurement data of a dual-source scan.

2. Calculate local measurement-spectrum-dependent weighting functions $\Omega_j(E,\vec{r})$ at the locations $\vec{r}$ of the examination object. Methods for calculating the local measurement-spectrum-dependent weighting functions are described in greater detail below.

3. According to the equation derived further below $$\bar{\mu}(\vec{r}) = \int_E \Omega(E, \vec{r}) \mu(E, \vec{r}) dE$$

a clear and measurement-spectrum-dependent relationship exists between the measured mean attenuation values $\bar{u}(\vec{r})$ and the energy-dependent and material-specific attenuation functions $\mu(E,\vec{r})$.

According to an embodiment of the invention, a list of potential attenuation functions $\mu_k(E,\vec{r})$ of previously selected reference materials is now tested for plausibility at the location $\vec{r}$, with the index k running over all tested materials, $k=1\ldots K$. In this case different criteria may be applied for the similarity between measurement and theoretical attenuation function. One possibility exists in determining the voxel-by-voxel deviation or—with reference to a larger cross-voxel area—the quadratic sum of the quadratic deviations between the determined local energy-dependent attenuation functions $\mu(E,\vec{r})$ and the theoretical values of the reference materials. As a result it may then be assumed that the reference material with the smallest deviation from the measurement is the most likely absorber at the location $\vec{r}$, therefore its occurrence is regarded as the most plausible. Alternatively, it is also possible for mixtures of the most probable materials at the location $\vec{r}$ to be taken into consideration. Thus, for example, an x-percentage probability of healthy tissue material and a (100−x) percentage probability of malignant tissue material.

The calculated material distributions may optionally also be subsequently iterated. For this purpose a more precise weighting function $\Omega_j(E, \vec{r})$ is calculated from the parameterized attenuation functions. Because of the lack of error sensitivity of the function $\Omega_j(E,\vec{r})$, in normal cases very few—one or two at the most—subsequent iterations are sufficient to obtain adequate approximations.

Finally, the calculated reference material distributions are displayed. Colored displays of the results may be selected for this, wherein the material, i.e. healthy, abnormal or malignant tissue, may be described by the choice of colors, for example. Concentrations calculated may additionally be displayed with the help of color intensity, and combined colors may also represent overlaid materials.

Thus a direct, qualitative identification of materials is facilitated, with the beam hardening being taken into account quantitatively.

Furthermore, new display options for CT data may be used and spatial filters may be employed to generate continuous material distributions and to increase confidence locally. In addition, malignant deviations from physical norms may be evaluated.

In accordance with these basic concepts the inventor proposes to improve the method known per se for preparing reconstructed CT image data records from $N \geq 2$ projection data records, recorded with N different spectral weightings $S_j(E)*D_j(E)$ in which j=1 to N, by defining the spectral weighting as the product function of the energy-dependent weighting of the radiation spectrum $S_j(E)$ used and the spectral sensitivity of a detector $D_j(E)$ that is used.

In at least one embodiment of this method, it is known for a CT scan to be carried out and N projection data records to be generated, each with a different spectral weighting $S_j(E)*D_j(E)$, and for N CT image data records to be reconstructed, each with a large number of local image values, which reflect local mean attenuation values $\bar{\mu}_j(\vec{r})$ at the location $\vec{r}$ of the examination object and of a measurement field, dependent upon the respective energy-dependent spectral weightings $S_j(E)*D_j(E)$ used for the scan.

An inventive improvement of at least one embodiment of the method provides for the following method steps:

establishing a first list of preferably $K \geq N$ reference materials with known mean attenuation values $\bar{\mu}_{i,j}$ in which j=1 to N and i=1 to K, which permit an initial approximate calculation of the beam hardening in the examination object, establishing a second list of preferably $M \geq N$ reference materials with known mean attenuation values $\bar{\mu}_{i,j}$ in which j=1 to N and i=1 to M, wherein preferably $M \geq K$, which may be present in the examination object, calculating a first approximate distribution of the reference materials in the examination object by comparing the previously calculated local mean attenuation values $\bar{\mu}_{i,j}(\vec{r})$ with the mean attenuation values from the first list of K reference materials $\bar{\mu}_{i,j}$, determining a distribution of local energy-dependent attenuation functions $\mu(E,\vec{r})$ in the examination object on the basis of the last known distribution of the reference materials and previously known material-specific energy-dependent attenuation functions $\mu_i(E,\vec{r})$ in which i=1 to M, calculating local measurement-spectrum-dependent weighting functions $\Omega_j(E,\vec{r})$ at the locations $\vec{r}$ of the examination object on the basis of the last known material distribution in the examination object with the associated material-specific energy-dependent attenuation functions $\mu(E,\vec{r})$, determining the distribution of local reference materials from the list of M reference materials according to plausibility principles over at least one specified region of interest in the examination object on the basis of the previously calculated local energy-dependent attenuation functions $\mu(E,\vec{r})$, and displaying the calculated distribution of the reference materials from the second list at least in the specified region of interest in the examination object.

For the plausibility consideration shown above, deviations between the measured local mean attenuation coefficients $\bar{u}_j(\vec{r})$ and the calculated local mean attenuation coefficients $$\int_E \Omega_i(E,\vec{r})\mu_j(E,\vec{r})dE$$

may—for example—be evaluated from the local energy-dependent attenuation functions $\mu(E,\vec{r})$ and the local measurement-spectrum-dependent weighting functions $\Omega_j(E,\vec{r})$ of the reference materials from the second list. In order to determine the deviations $\Delta_j$ the equation $$\Delta_j = \sum_{i=1}^{M}\left(\bar{\mu}_i(\vec{r}) - \int_E \Omega_i(E,\vec{r})\mu_j(E,\vec{r})dE\right)^2$$

may be used, wherein j represents the index for the reference material. The plausibility for the presence of a j-th material at the observed location may therefore be compared with the probability $P_j$ and calculated as $$P_j = \frac{\Delta_j}{\sum_{j=1}^{N}\Delta_j}.$$

It should be noted in this context that the described calculations in no way represent the only possible approaches with regard to plausibility. Thus other calculation and comparison methods that are known per se from statistics may be used. In particular, the possibility also exists for previous knowledge with regard to potential spatial distributions or neighboring conditions be brought to bear.

Essentially, once the embodiment of the inventive method described above has been carried out, an image is available which shows a highly detailed distribution of the reference materials. If this distribution is to be improved further, however, then the option exists to go over to an iterative method, in which the following stages:

calculating local measurement-spectrum-dependent weighting functions $\Omega_j(E,\vec{r})$ at the locations $\vec{r}$ of the examination object on the basis of the last known material distribution in the examination object with the associated material-specific energy-dependent attenuation functions $\mu(E,\vec{r})$, and determining the distribution of local reference materials from the list of M reference materials according to plausibility principles over at least one specified region of interest in the examination object on the basis of the previously calculated local energy-dependent attenuation functions $\mu(E,\vec{r})$, may be iterated several times and—after the end of the iterations or even as an interim result—a tomographical image of the calculated distribution of the reference materials from the second list, at least in the specified region of interest in the examination object, is shown.

In specific terms, in this method for calculating the measurement-spectrum-dependent local weighting functions $\Omega(E,\vec{r})$ at the locations $\vec{r}$ of the examination object, the equation $$\Omega(E,\vec{r}) = w(E,\vec{r})\frac{\bar{\mu}(\vec{r})}{\mu(E,\vec{r})}$$

may be used in which:

$$\bar{\mu}(\vec{r}) = R^{-1}\{P\{\mu(E,\vec{r})\}\}$$
$$\text{and } w(E) = \frac{S(E)D(E)}{\int_E S(E')D(E')dE'},$$

wherein P is the forward projection operator in a reconstruction of a CT image data record and $R^{-1}$ is the inverse radon transformation operator in a reconstruction of a CT image data record.

This method may be used to particular advantage in the field of medical diagnostics, in which case a patient is the examination object.

In this case it is favorable if the first list of reference materials contains a selection of two to four materials from the following list: water, tissue, bone, air and contrast medium. In this case a combination of a few materials that may be unequivocally differentiated at the mean attenuation values of a simple CT image, such as water and bone, are used, which permits a good initial estimate of the local measurement-spectrum-dependent weighting functions or values $\Omega_j(E,\vec{r})$.

The second list of reference materials may advantageously contain a selection of two to four materials from the following list: water, tissue, bone, air and contrast medium. If, however, certain materials such as—for example—healthy organ-specific tissue and malignant organ-specific tissue of a particular organ are being sought specifically, then these may be included in the second list. In this case it may also be particularly advantageous for the area of particular interest, for example a specific organ, to be delimited by manual input or segmentation algorithms and subsequently for the inventive method or iteration method to be executed again specifically on this area, using a second list of reference materials that contains only the materials being sought. Other previously defined areas of the patient remain unaffected by this, however, and are taken into account in the method without altering the calculated material distribution.

The method described above may also be used on inanimate objects. In this case, it is possible for only the materials processed in the examination object to be used in the first and second list of reference materials. Furthermore, the first and second list of reference materials may be differentiated whereby at least one material sought in the object is used in the second list.

With regard to the generation of initial CT image data with different energy-dependent spectral weightings $S_j(E)*D_j(E)$, it is proposed that this be achieved by the use of different radiation spectra and/or by the use of different spectral detector sensitivities.

The scope of at least one embodiment of the invention also includes a CT system for scanning an examination object, comprising a control and processing unit with a memory for computer program code, wherein computer program code is stored in the memory and the processor can execute at least one embodiment of the inventive method whilst in operation.

Embodiments of the invention is described in greater detail below with the help of diagrams, in which only those features that are necessary to the understanding of the invention are shown. The following reference characters and abbreviations are used: 1: CT system; 2: First x-ray tube; 3: First detector; 4: Second x-ray tube (optional); 5: Second detector (optional); 6: Gantry housing; 6.1: Swivel arm; 7: Examination object/Patient/Phantom; 7.1: Region of particular interest/ROI; 8: Examination couch; 9: System axis; 10: Control unit and processor with optional additional ECG function; 11: Contrast medium dispenser; 12: ECG cable; 13: C-arm system; 16.1 to 16.8: Method steps; 17.1: First list; 17.2: Second list; A: Attenuation; D: Detector; d: Length of projection path through object area; D(E): Spectral sensitivity of detector with energy E; E: Energy; I: Radiation intensity; $I_0$: Radiation intensity without attenuation; k: Constant; L: Projection path; MF: Measurement field; $M_{1-x}$: Materials on the first list; $M_{2-x}$: Materials on the second list; O: Object; P1 to P3: Measurement points; $Prg_1$-$Prg_n$: Computer programs; S: Radiation source; $S_1$ to $S_7$: Method steps; S(E): Weighting of the radiation spectrum at energy E; w(E): Weighting function; Z: Atomic number; Δ: Deviation; γ: X-ray beam; θ: Projection angle; c($\vec{r}$): Local partial density; $\vec{r}$, $\vec{r}'$: Location coordinates; μ(E,$\vec{r}$): Local energy-dependent attenuation function; $\bar{\mu}_j(\vec{r})$: Local mean attenuation coefficient; Ω(E,$\vec{r}$): Local measurement-spectrum-dependent weighting function.

Indexing is used by consensus.

BRIEF DESCRIPTION OF THE DRAWINGS

In detail, the diagrams are as follows.

DETAILED DESCRIPTION OF THE EXAMPLE EMBODIMENTS

Figure 1:
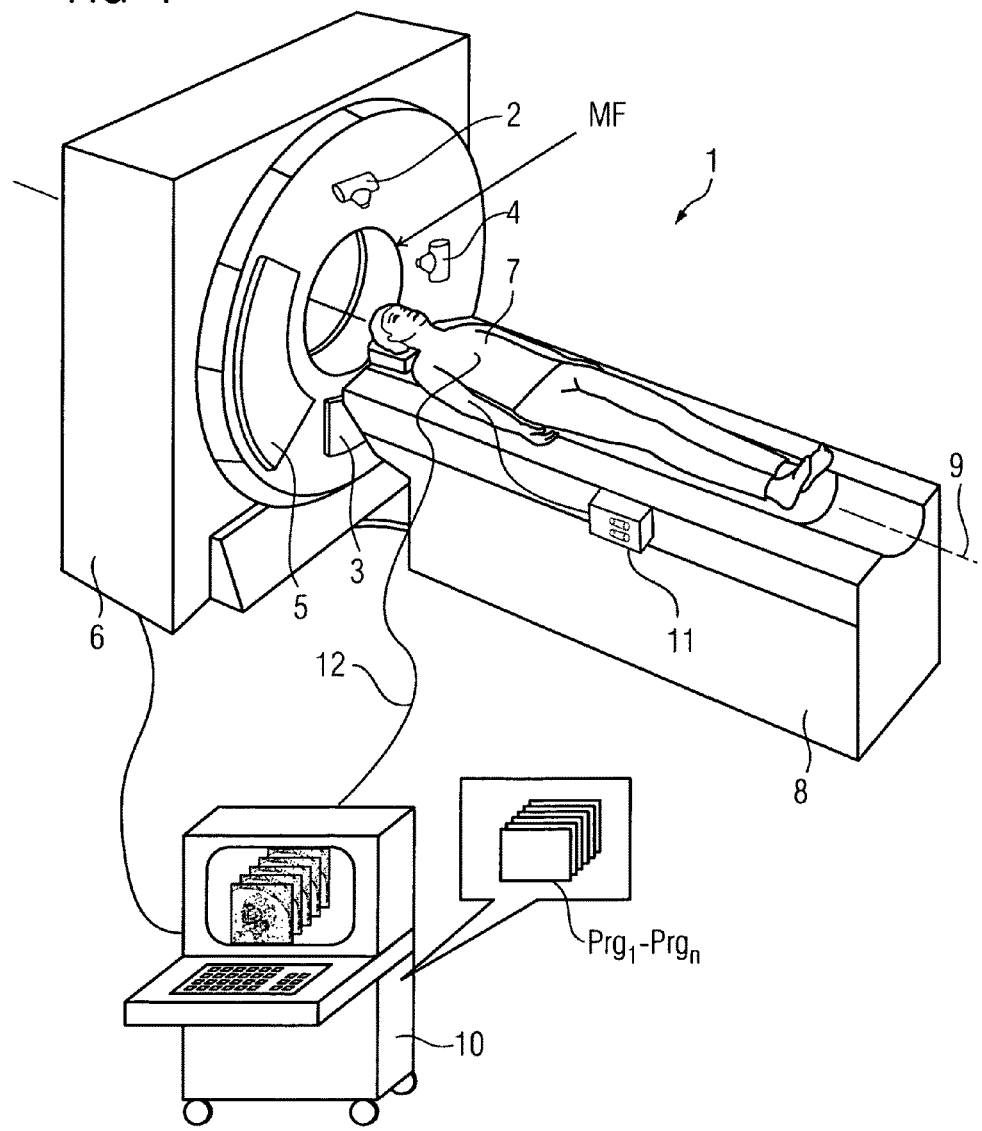
FIG. 1: CT system for implementing an embodiment of the inventive method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an inventive CT system 1 with which an embodiment of the inventive method may be implemented. The CT system 1 has a first tube/detector system with an x-ray tube 2 and a detector 3 located opposite. This CT system 1 may optionally have a second x-ray tube 4 with a detector 5 located opposite. Both tube/detector systems are disposed on a gantry, which is arranged in a gantry housing 6 and rotates around a system axis 9 during scanning. The patient 7 is situated on a movable examination couch 8, which is either continuously or sequentially pushed along the system axis 9 through the measurement field MF located in the gantry housing 6, during which process the attenuation of the x-ray radiation emitted by the x-ray tubes is measured by the detectors.

During the measurement the patient 7 may also be injected with a contrast medium bolus with the help of a contrast medium dispenser 11, so that blood vessels may be more easily detected or a perfusion measurement carried out. In the case of cardiac recordings it is also possible, with the help of an ECG cable 12, for cardiac activity to be measured and an ECG-gated scan to be carried out.

The CT system is controlled with the help of a control unit and processor 10, in which computer programs $Prg_1$ to $Prg_n$ are located. Said programs can also implement the inventive method described above. In addition, this control unit and processor 10 can also display image data.

In this CT system, with two separate x-ray sources, it is possible—for example—for one x-ray tube to be operated with an accelerating voltage of 80 kVp and the other x-ray tube with 140 kVp. This causes different spectral weightings to be produced during measurements, which—if the detectors used have the same spectral sensitivity—come from the different x-ray spectra of the two x-ray tubes. Alternatively, however, it is also possible for both x-ray tubes to use the same radiation spectrum, but to provide for different spectral sensitivity of the detectors. A combination of the two measures is also possible.

Figure 2:
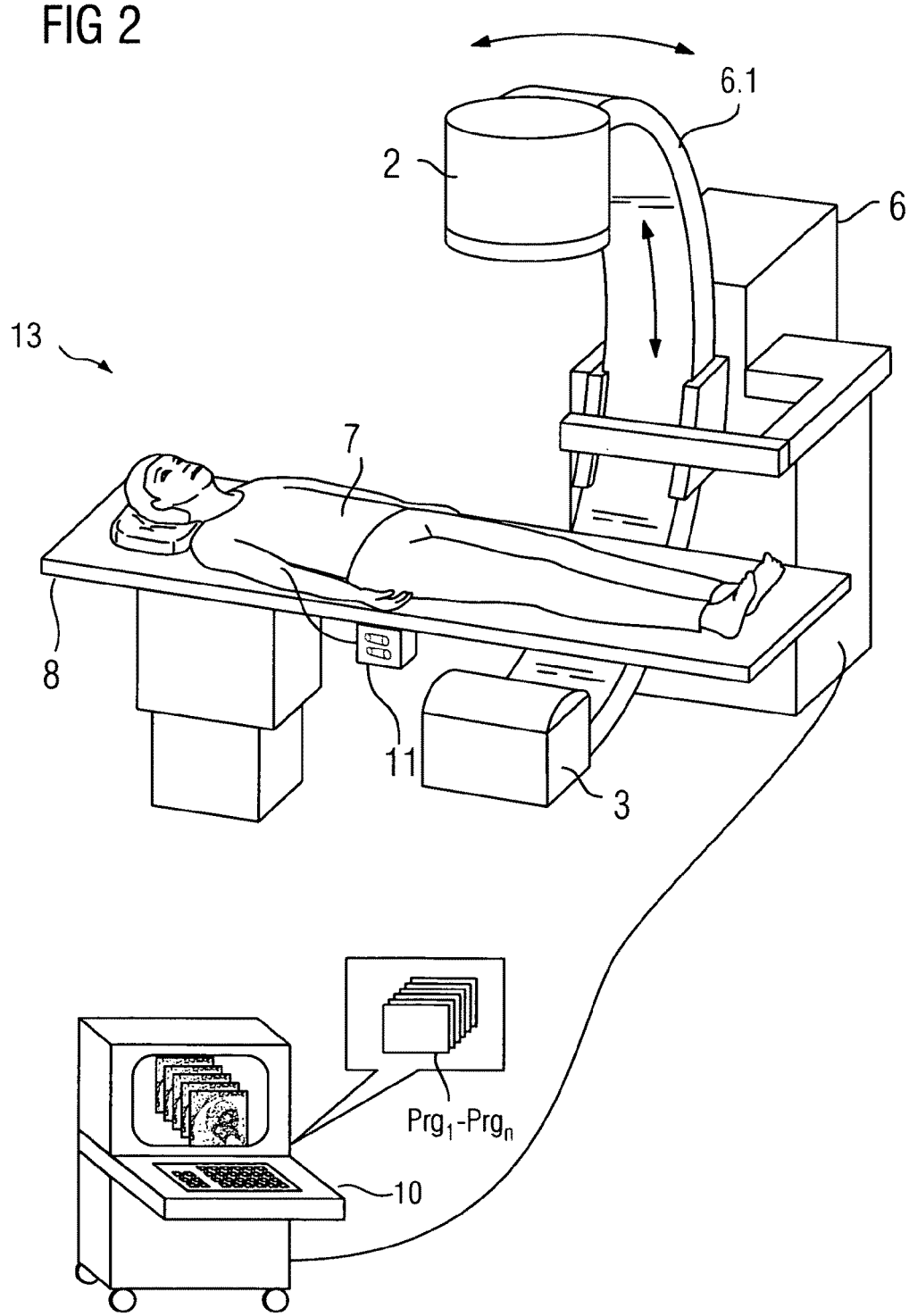
FIG. 2: C-arm system for implementing an embodiment of the inventive method.

An embodiment of the inventive method may also be used in combination with a C-arm system 13, as shown in FIG. 2. The C-arm system 13 shown here likewise has an x-ray tube 2 with a flat-designed detector 3 located opposite. With the help of a swivel arm 6.1, which is mounted on a housing 6, the two systems are able to swing around the patient 7 in any position and scan a measurement field. The patient 7 is situated on a couch 8, which additionally has a contrast medium dispensing system 11 for injecting contrast medium as necessary in order to display blood vessels. The system is controlled via a control unit and processor 10, which has computer programs $Prg_1$ to $Prg_n$ in its memory, said programs also being able—among other things—to implement the inventive method for image processing. Measurements with different spectral weightings may, for example, be realized using an energy-specific detector system.

Both of the systems described above are suitable for implementing the inventive method, the principles of which are now described.

Figure 3:
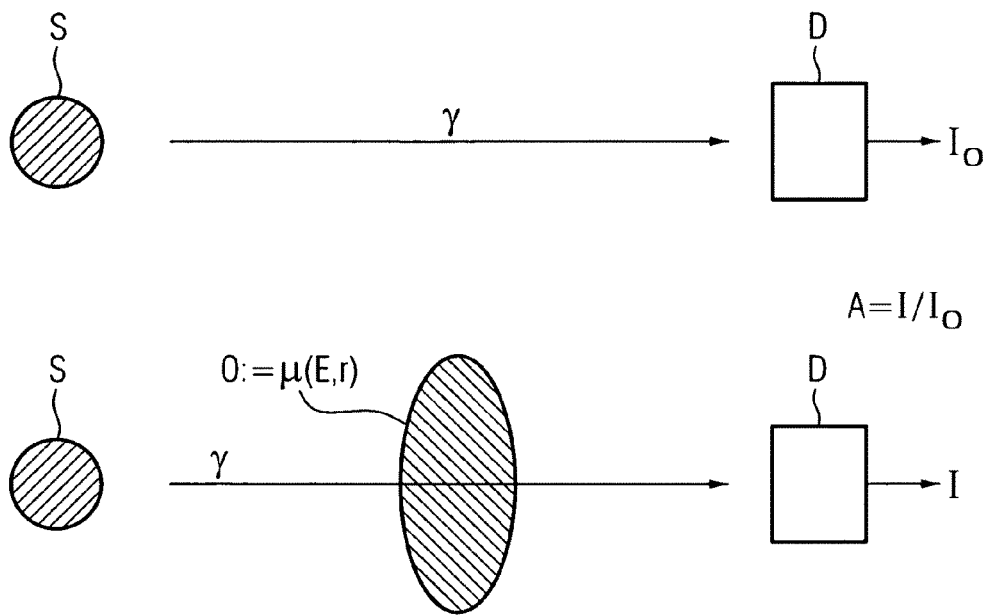
FIG. 3: Schematic diagram showing the attenuation measurement of a radiation beam.

FIG. 3 schematically illustrates the standard structure of an x-ray beam attenuation measurement. An x-ray source S is shown, which emits an x-ray beam to a detector D. In the upper part the path of an x-ray beam γ from the source S to the detector D is free and a radiation intensity $I_0$ is measured. In the lower part of FIG. 3 an object O is located in the path of the beam, causing the radiation to be attenuated, so that a lower intensity I is measured at the detector D.

Figure 4:
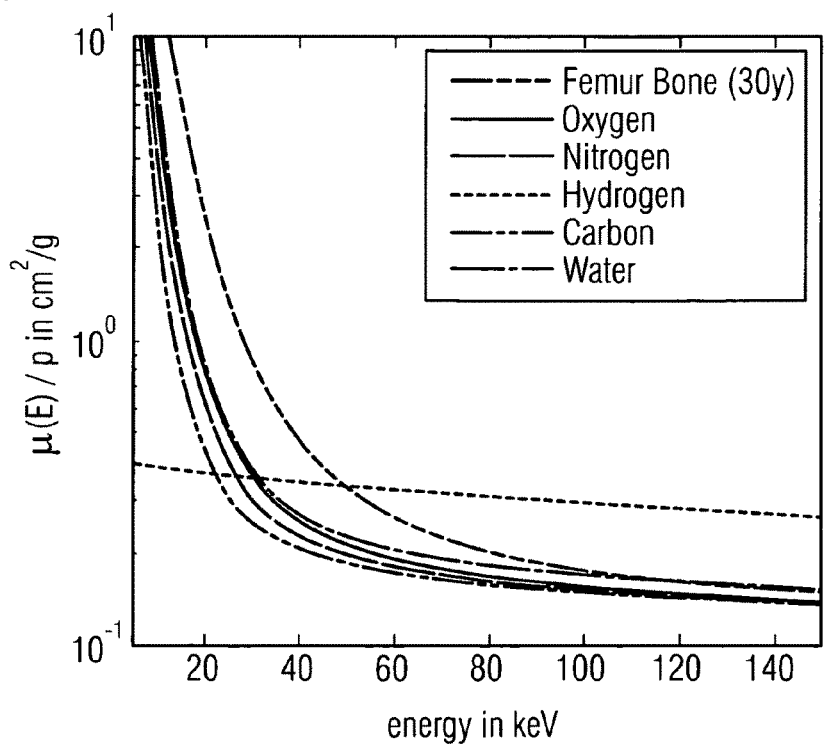
FIG. 4: Value pattern of energy-dependent specific attenuation functions μ(E,$\vec{r}$) over energy (=basic functions)

The attenuation $A=I/I_0$ is described by the energy-dependent attenuation function $\mu(E,\vec{r})$ with reference to the energy E used at the location $\vec{r}$. Typical examples of materials for $\mu(E,\vec{r})$ are shown in FIG. 4 by way of example.

The detector D therefore registers the quanta emitted from the object. One measurement is taken with the object and one without the object. The attenuation $A=I/I_0 \in [0;1]$ is derived from the resulting intensities I and $I_0$. It thus describes the relative decrease in intensity caused by the x-ray radiation attenuation process in the object.

It is necessary here to differentiate between monoenergetic and polychromatic x-ray sources S.

a) For monoenergetic source energy $E_0$ of the x-ray quanta the attenuation is $A^{(m)}$ $$A^{(m)} = \frac{I}{I_0} = \exp\left(-\int_{[L]} \bar{\mu}^{(m)}(\vec{r}) d\vec{r}\right) \quad (1)$$

Figure 5:
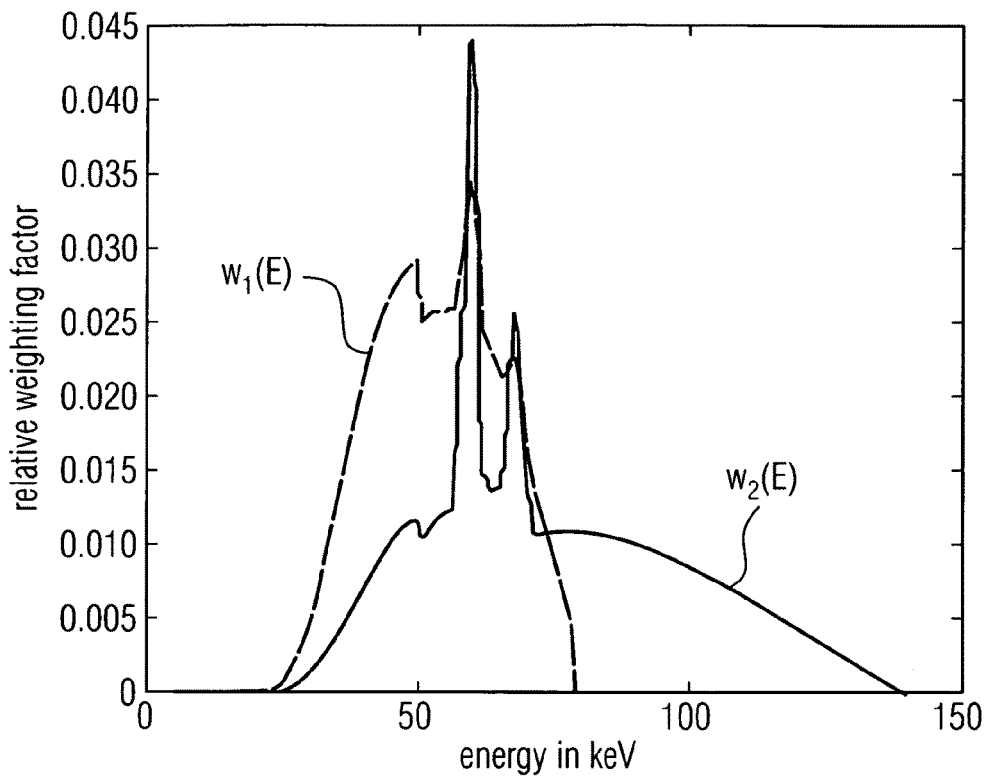
FIG. 5: Progression of two energy-dependent weightings of radiation spectra $S_j(E)$ over energy.

In this case the monoenergetic attenuation coefficient $\bar{\mu}^{(m)}(\vec{r})$ is equivalent to $\mu(E,\vec{r})$.

b) For polychromatic x-ray sources, which x-ray tubes in general are, a spectrum, or—more precisely—a spectral weighting S(E) of a radiation spectrum is used for the source power. Two exemplary spectra are shown in FIG. 5 for an x-ray tube with 80 kVp and an x-ray tube with 140 kVp. The measured attenuation A is thus calculated according to the following equation $$A = \frac{I}{I_0} \\
= \frac{\int_E S(E)D(E)\exp\left(-\int_{\{L\}}\mu(E,\vec{r})d\vec{r}\right)dE}{\int_E S(E)D(E)dE} \\
= \int_E w(E)\exp\left(-\int_{\{L\}}\mu(E,\vec{r})d\vec{r}\right)dE \quad (2)$$

with the spectral weighting function $$w(E) = \frac{S(E)D(E)}{\int_{E'} S(E')D(E')dE'} \quad (3)$$

Figure 6:
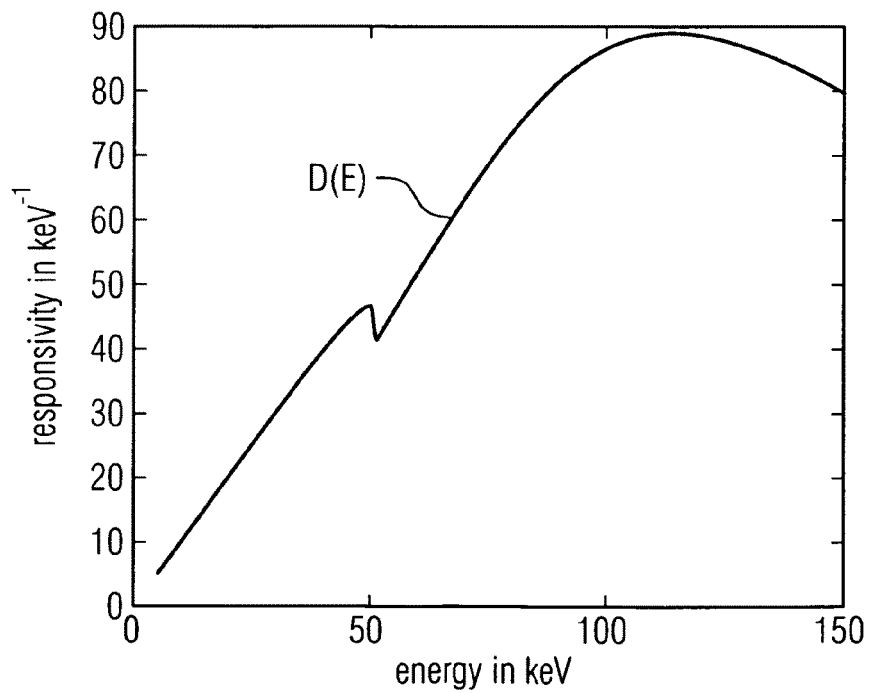
FIG. 6: Progression of spectral sensitivity of an exemplary detector $D_j(E)$ over energy.
Figure 7:
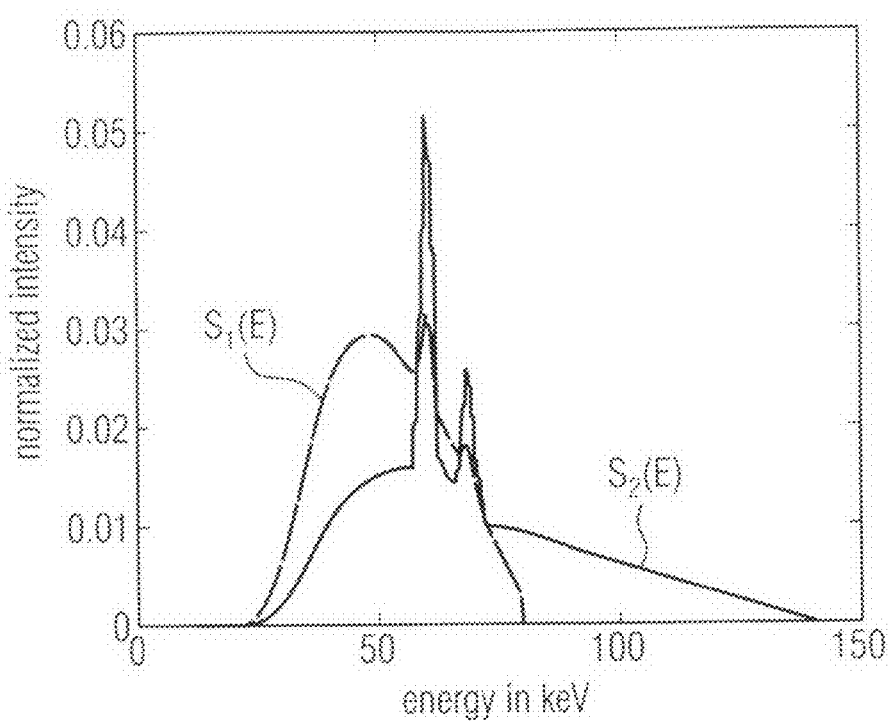
FIG. 7: Progression of two energy-dependent spectral weightings $S_j(E)*D_j(E)$ for each radiation detector combination over energy.

The detector sensitivity D(E) here describes the spectral weighting of the detector. For a detector to be ideally integrated it may be assumed that D(E)=E. However, detectors suitable for these measurements have a very costly structure and must be precisely calculated or measured out. A typical sensitivity process D(E) of a $Gd_2O_2S$ scintillation detector, as is generally used in conjunction with commercial CT systems, is shown in FIG. 6. FIG. 7 shows the spectral weighting function w(E) with S(E) and D(E) from FIGS. 5 and 6, calculated according to equation (3), Medical and industrial CT systems normally use x-ray tubes as the emission source. FIG. 5 shows the typical spectra for acceleration voltages of 80 kVp and 140 kVp in a system used for medical purposes. The CT measurement process for generation of projection data is correctly described with the equation (2). However, in standard CT measurements, energy-resolved attenuation values are not measured, but attenuations integrated via the energy are determined over the entire spectrum. Nor can any image data that displays $\mu(E,\vec{r})$ as image values be calculated from this. Spectrally resolved sinogram data records $A_t(E)$ would be required for this purpose.

Figure 12:
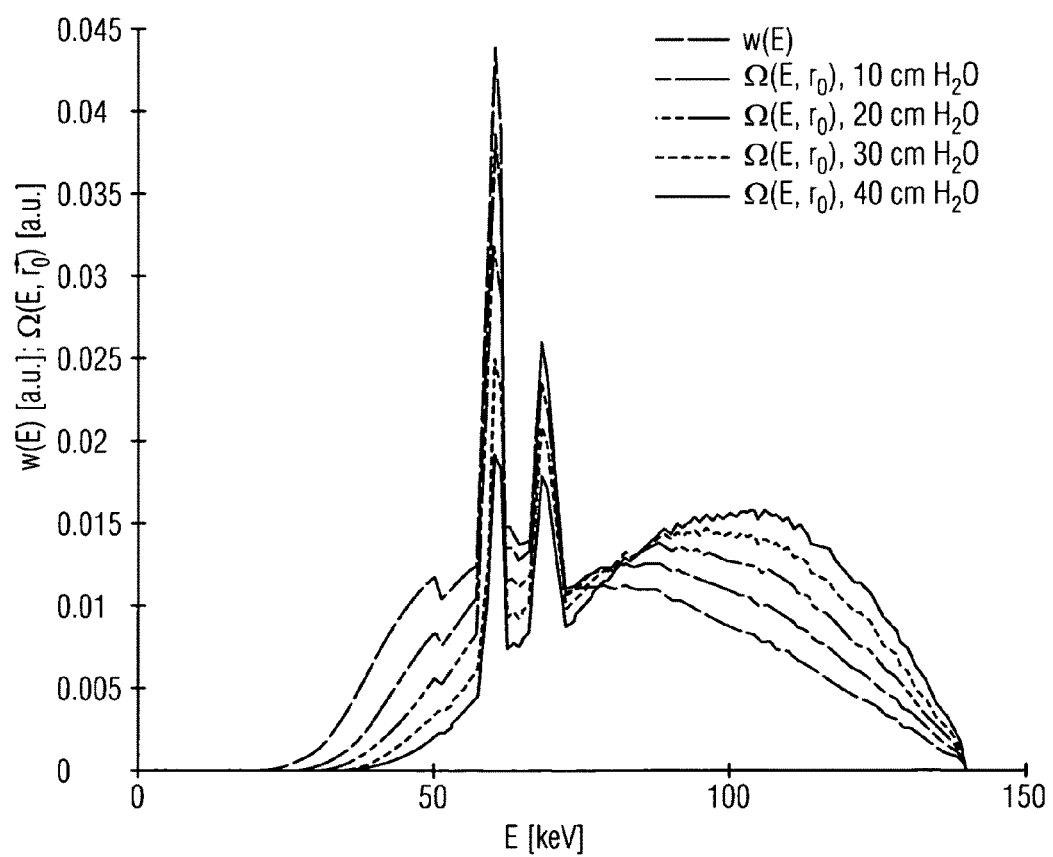
FIG. 12: Various local measurement-spectrum-dependent weighting functions Ω(E,$\vec{r}_0$) dependent upon a penetrated water layer with the initial spectral weighting w(E) of the radiation spectrum used.

In single-energy CT, this conflict leads to a normal approximation. The radon transformation and its inverse are based on the physical principles of linear x-radiation, in order to reconstruct the local spectrally weighted attenuation coefficients $\bar{\mu}(\vec{r})$ of the examination object. The errors from the estimation are usually known as "beam hardening artifacts". The model used as the basis requires that the equation (1) is to be used as an estimate. For the x-radiation that passes through the object, a mean detected energy <E> is assumed. If the x-ray quanta pass through thick areas or areas with a high atomic number Z, such as bone, for example, this mean energy of the detected x-ray quanta increases by a few keV depending on the attenuation characteristics. FIG. 12 shows the hardening of the radiation spectrum and thus also the mean energy of an x-ray beam depending on water layers of varying thickness. The beam spectrum is therefore "hardened" and reconstructed $\bar{\mu}(\vec{r})$ of the mean energy <E> of the primary spectrum S(E) are consequently understand.

The errors in estimation may be analytically determined. It may be seen that equation (2) can also be written as follows:

$$A = \exp\left(-\int_{\{L\}}\bar{\mu}(\vec{r})d\vec{r} + R\right) \quad (4)$$

Using the error term $$R = \frac{1}{2}\int_E w(E)\left(\int_{\{L\}}\mu(E,\vec{r})d\vec{r}\right)^2 dE + \text{(higher order terms)} \quad (5)$$

the spectrally weighted attenuation coefficient may be described as follow:

$$\bar{\mu}(\vec{r}) = \int_E w(E)\mu(E,\vec{r})dE. \quad (6)$$

Figure 8:
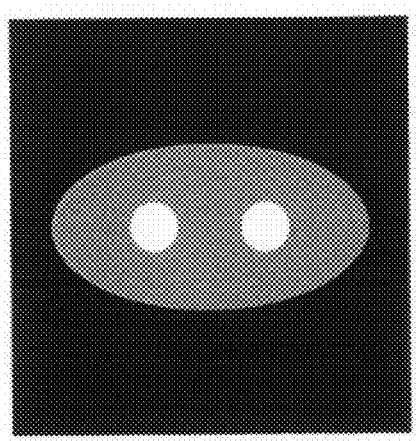
FIG. 8: Image of a phantom with actual attenuation values.
Figure 9:
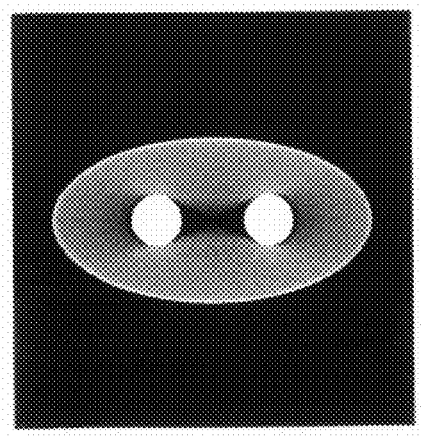
FIG. 9: CT image of the phantom from FIG. 8 with beam hardening artifacts.

The first-order error R from equation (4) leads to an overestimation of A and a consequent underestimation of the weighted attenuation coefficient $\bar{\mu}(\vec{r})$ in the reconstructed image. FIG. 9 shows a typical example of a CT image of a phantom shown in FIG. 8 in medical CT. The CT image of the phantom shows the known typical beam hardening artifacts of cupping and a "tunnel effect" between the bone phantoms.

Known beam hardening corrections alleviate these artifacts in practical single-energy CT by correcting the measured attenuation $A_t$, wherein the length of the attenuating material in the path of the beam is calculated and the resulting energy displacement is compared to the mean energy. This algorithm normally enables good results to be achieved in the display of soft tissue in medical CTs. However, such measures are not intended to achieve absolute quantitative accuracy of reconstructed CT values.

Figure 10:
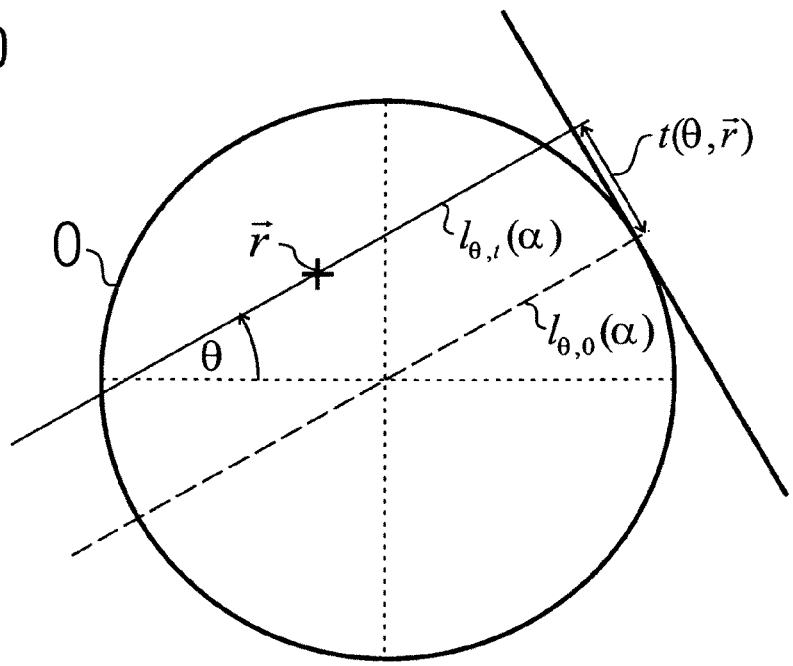
FIG. 10: Schematic diagram of an object O with two penetrating x-ray beams γ in the projection angle θ and with distance t(θ,r)

FIG. 10 shows a standard projection geometry in a CT system. In parallel projection geometry, a beam is described by the projection angle θ and its channel separation to the midpoint of the CT detector. This results in the typical projection formula $$P\{\mu(E,\vec{r})\} = -\ln\left(\int_0^\infty w(E)\exp(-M_{\theta,t}(E))dE\right) \quad (7)$$

with the forward projection operator P{.} and the abbreviation of the spatial path integration $$M_{\theta,t}(E) = \int_{-\infty}^\infty \mu(E, l_{\theta,t}(\alpha))d\alpha \quad (8)$$

with $l_{\theta,t}(\alpha)$ being the projection path through the object to the rotation angle θ, the detector channel being t and the linear parameter α for the path integration.

The reconstructed local mean attenuation coefficient is shown as $$\bar{\mu}(\vec{r}) = R^{-1}\{P\{\mu(E,\vec{r})\}\} \quad (9)$$

with the inverse radon transformation operator $R^{-1}\{.\}$.

Using a factor $$1 = \int_0^\infty w(E)dE$$

in the equation (9) and taking into account the condition that $P\{\mu(E,\vec{r})\}$ is independent of E gives the equation $$\bar{\mu}(\vec{r}) = \int_0^\infty w(E)R^{-1}\{P\{\mu(E,\vec{r})\}\}dE \quad (10)$$

Expansion of the equation (10) by the factor $$\frac{\mu(E,\vec{r})}{\mu(E,\vec{r})}$$

gives $$\bar{\mu}(\vec{r}) = \int_0^\infty w(E)\frac{R^{-1}\{P\{\mu(E,\vec{r})\}\}}{\mu(E,\vec{r})}\mu(E,\vec{r})dE. \quad (11)$$

This expression may be reformulated as $$\bar{\mu}(\vec{r}) = \int_0^\infty \Omega(E,\vec{r})\mu(E,\vec{r})dE \quad (12)$$

with the local weighting function $$\Omega(E,\vec{r}) = w(E)\frac{R^{-1}\{P\{\mu(E,\vec{r})\}\}}{\mu(E,\vec{r})}. \quad (13)$$

The equation (11) thus links the spectral attenuation function $\mu(E,\vec{r})$ with the measured, weighted attenuation coefficient $\bar{\mu}(\vec{r})$. This results in a description, based on image data, of the measurement process in the CT and of the reconstruction process.

The local weighting function $\Omega(E,\vec{r})$ from equation (13) describes the effective spectral weighting at a desired object position. It is dependent upon the spectral attenuation function of the scanned object $\mu(E,\vec{r})$, the image data reconstruction process $R^{-1}\{.\}$ and the measurement process, which is described by the operator $P\{.\}$. The weighting function $w(E)$ is produced from the weighting function of the system in equation (3).

In practical CT application, only weighted attenuation coefficients $\bar{\mu}(\vec{r})$ are measured. In order to calculate the local weighting function, an estimate of the spectral attenuation functions $\mu(E,\vec{r})$ depending on input data is required. A dual-energy scan results in two attenuation data records $\bar{\mu}_1(\vec{r})$ and $\bar{\mu}_2(\vec{r})$. Basic material decomposition is used in a form to be based on image data records, in order to obtain the parameterization of $\mu(E,\vec{r})$. This approach is described by $$\mu(E,\vec{r}) = \sum_{j=1}^M c_j(\vec{r})f_j(E). \quad (14)$$

This expression separates the energy-dependent basic function $f_j(E)$ from the location-dependent coefficients $c_j(\vec{r})$. The typical values of the basic function in the medical application of CT is a combination of the measurement-dependent attenuation functions of water and bone. Equation (12) produces the following:

$$\begin{pmatrix}\bar{\mu}_1(\vec{r})\\ \bar{\mu}_2(\vec{r})\end{pmatrix} = K\begin{pmatrix}c_1(\vec{r})\\ c_2(\vec{r})\end{pmatrix}, \quad (15)$$

wherein the elements of the matrix K are expressed as $$K_{i,j} = \int_E \Omega_i(E)f_j(E)dE. \quad (16)$$

Figure 11:
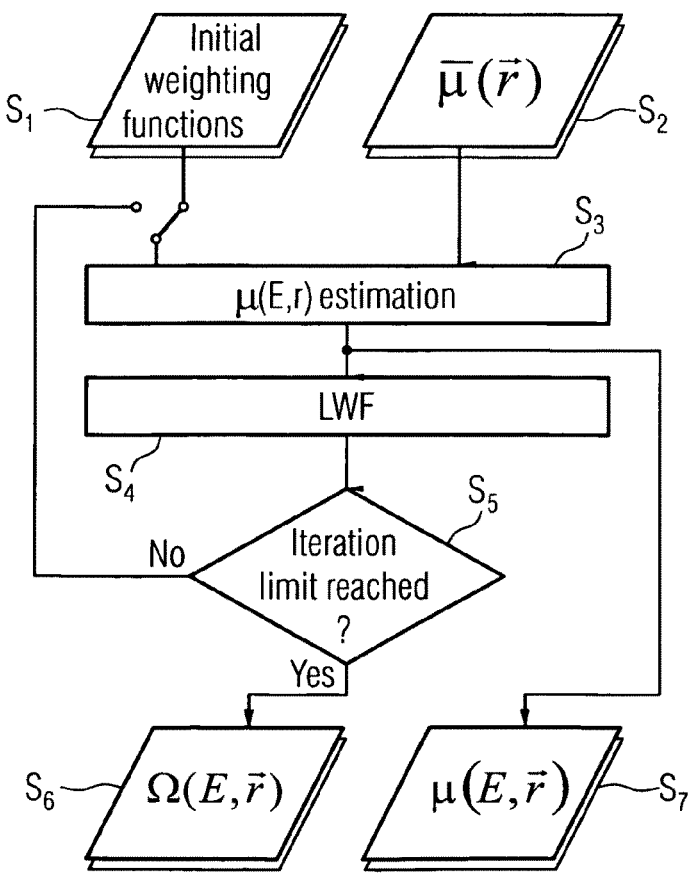
FIG. 11: Flowchart showing an embodiment of the inventive LSR method.

The equation (15) is easily solved with the coefficients $c_j(\vec{r})$ by inverting the matrix K. However, the circular dependencies $K \to c_j(\vec{r}) \to \mu(E,\vec{r}) \to \Omega_i(E,\vec{r}) \to K$ must also be solved. This leads to a two-phase iterative process according to the flow chart in FIG. 11. In this process, the initial local weighting function is first estimated in method step $S_1$, in which $\Omega_i^{(k=0)}(E,\vec{r}) = w(E)$ is set. By way of example, this may be estimated in method step $S_2$ from the knowledge of the existing CT image which is likewise available at the start, with the measured and reconstructed mean local attenuation coefficients $\bar{\mu}(\vec{r})$. From the two results of steps S1 and S2 are derived an initial estimation of the local mass attenuation functions $\mu(E,\vec{r})$ in step $S_3$. This results in the calculation of the local weighting functions $\Omega(E,\vec{r})$ in step $S_4$. In addition, from the knowledge of the local mass attenuation functions $\mu(E,\vec{r})$ and a predefined desired spectrum, in step $S_7$ it is possible in an inventive manner for the local weighted attenuation coefficients of the observed object to be calculated with regard to any assumed spectrum and displayed as a CT image. If the method for optimization is performed repeatedly, then these steps may be repeated as often as required following a decision in step $S_5$ according to the flow chart shown, with the last local weighting function to be calculated being displayed in step $S_6$. In this way the estimation of $\mu_i^{(k)}(E,\vec{r})$ and $\Omega_i^{(k)}(E,\vec{r})$ is repeated at every k-th iteration stage.

This method is referred to here as Local Spectral Reconstruction (LSR). It results in an estimate both of the local weighting function and of the attenuation functions $\mu(E,\vec{r})$. The LSR method may be transferred to spectral multichannel CT and basic material decomposition, for example if there is a quantity of N>2 spectral channels and a quantity of M<=N basic materials. For single-energy CT, $\mu(E,\vec{r})$ may be estimated from an energy-weighted effective attenuation coefficient $\bar{\mu}(\vec{r})$.

From the LSR method according to equations (12) and (13) is derived an estimation both of the local weighting function and of the actual accuracy of the spectral attenuation functions $\mu(E,\vec{r})$ of the object. The information from the local weighting function provides a deeper understanding of the energy weighting process in CT imaging. For quantitative use of the spectral CT, the attenuation functions $\mu(E,\vec{r})$ obtained as a result are the main outcome. The associated parameters such as basic material coefficients may be graphically displayed or analyzed for specific diagnostic interrogations.

It is important to note that the attenuation function $\mu(E,\vec{r})$ is theoretically unaffected by the attenuation effects of the object, the characteristics of the reconstruction and the measurement process. Therefore, for example, the core of the reconstruction of dual-energy measurements may be taken into account. Pixel registration between the data records may be improved as a result of this.

In practice, exact descriptions of the weighting function $w(E)$ and of the measurement operator $P\{.\}$ are necessary in order to guarantee quantitative results. It should be noted that both the image reconstruction and the calculation of the local weighting function result from the reconstruction operator $R^{-1}\{.\}$. Apart from this there are no further effects with regard to accuracy and precision of $\mu(E,\vec{r})$.

Essentially, there are a few different objectives of the inventive weighting presented above:

It may be used for beam hardening corrections, in order—for example—to obtain a constant system weighting function (SWF) of an image data record, as shown in FIG. 5 for $w(E)$ of a CT measurement for 80 kVp and 140 kVp tube voltage.

Furthermore, monoenergetic calibrations may be carried out with a target weighting function specified by $w_c(E)=\delta(E-E_0)$. One application of these monoenergetic attenuation coefficients is increased contrast in image differences of special tissue.

The local spectral weighting function $\Omega(E,\vec{r})$ therefore describes, for each location $\vec{r}$ of the reconstructed image data from the weighted local attenuation values $\bar{\mu}(\vec{r})$ the spectral weighting effective there. It forms the average of the spectral weightings of the tomographical scanning paths that are present upon generation of the relevant $\bar{\mu}(\vec{r})$ data. $\Omega(E,\vec{r})$ may be calculated accurately from the energy-dependent attenuation functions $\mu(E,\vec{r})$.

Equation (12) links the reconstructed image data reflected by the local spectrally weighted attenuation coefficients $\bar{\mu}(\vec{r})$ with the energy-dependent attenuation functions $\mu(E,\vec{r})$. The structure of equation (12) is similar to the result of the linear estimation. The global weighting function $w(E)$ is thus replaced by the local weighting function $\Omega(E,\vec{r})$. Equation (12) is an exact formula per se, though it does have intrinsic characteristics, for example the local weighting function $\Omega(E,\vec{r})$ requires knowledge of $\mu(E,\vec{r})$ of the entire object.

The local weighting function $\Omega(E,\vec{r})$ may be calculated from a volume integral via $\mu(E,\vec{r})$ in polar or Cartesian coordinates.

If, for example, the local weighting function $\Omega(E,\vec{r})$ is calculated in the center $r_0$ of an aqueous object with a specific diameter, in which the 140 kVp spectrum of an x-ray tube as per FIG. 7 and the spectral sensitivity $D(E)$ of a GdOS detector to be integrated as per FIG. 6 is taken as the radiation spectrum $S_2(E)$, this results in a $\Omega(E,\vec{r}_0)$ as shown in FIG. 12 for different diameters of the aqueous object. As the diameter increases, in this case 10 cm, 20 cm, 30 cm and 40 cm, the energy weighting $\Omega(E,\vec{r}_0)$ moves to higher energies.

A spectral reconstruction is carried out as follows.

1. Spectral Measurement

J CT measurements are carried out with different spectral weightings $w_j(E), j=1, 2, \ldots J$. For example, these may be dual-energy scans (J=2) with an x-ray tube setting of 80 kVp and 140 kVp for two separate scans. The resulting sinograms may be reconstructed into image data records with the help of generally known reconstruction algorithms, for example a filtered back projection. This produces J different image data records from the local spectrally weighted and measurement-spectrum-dependent attenuation values $\bar{\mu}_j(\vec{r})$. The reconstructed data records contain beam hardening effects.

2. Calculation of Local Attenuation

In order to calculate the weighting functions $\Omega(E,\vec{r})$, the x-ray tube spectrum $S(E)$, the detector response function $D(E)$ and the initial estimate of the energy-dependent attenuation function $\mu^{(0)}(E,\vec{r})$ are required. The index $^{(0)}$ here stands for the $0^{th}$ iteration. Both the x-ray tube spectrum $S(E)$ and the detector response function $D(E)$ may be obtained from simulations or direct measurements with a calibrated detector.

The initial estimate of the energy-dependent attenuation function $\mu^{(0)}(E,\vec{r})$ may be estimated from the image data records from step 1. In medical CTs, for example, a separation into two main attenuations—for example water and bone—may be generated by a segmentation by means of threshold value formation of $\bar{\mu}_j(\vec{r})$ or a basic material decomposition. The resulting initial attenuation produces a first estimate of weighting functions $\Omega^{(0)}(E,\vec{r})$ in accordance with the equations (11) and (12).

3. Reconstruction of Local Energy-Dependent Attenuation Function

Together with $\bar{\mu}_j(\vec{r})$ from step 1 and $\Omega^{(0)}(E,\vec{r})$ from step 2, the parameterization of the energy-dependent attenuation function $\mu^{(1)}(E,\vec{r})$ may be calculated from equation (13). A basic material decomposition which is known per se is used for this purpose, although on the basis of the attenuation function $\mu^{(1)}(E,\vec{r})$, which is independent of the measured radiation and its spectrum and spectral weighting in the detector, and is thus measurement spectrum-independent. For example, a dual-energy basic material decomposition M=2 generates concentrations of water and bone.

4. Iteration

With the more precise information, by comparison to $\mu^{(0)}(E,\vec{r})$, about the local energy-dependent attenuation functions $\mu^{(1)}(E,\vec{r})$ from step 3, it is possible to return to step 2 and to calculate a current value $\Omega^{(1)}(E,\vec{r})$. This results in a continuous iterative process. Because of the slowly varying and error-tolerant mathematical structure of $\Omega(E,\vec{r})$, the number of iteration steps is low. One or two iterations are sufficient in practice.

Figure 13:
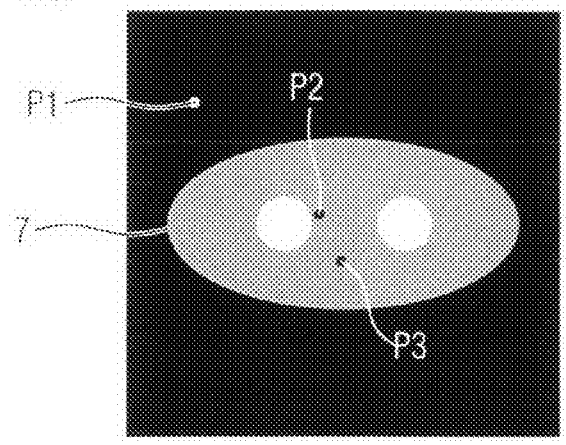
FIG. 13: CT image of a phantom with 3 measurement points P1-P3.
Figure 14:
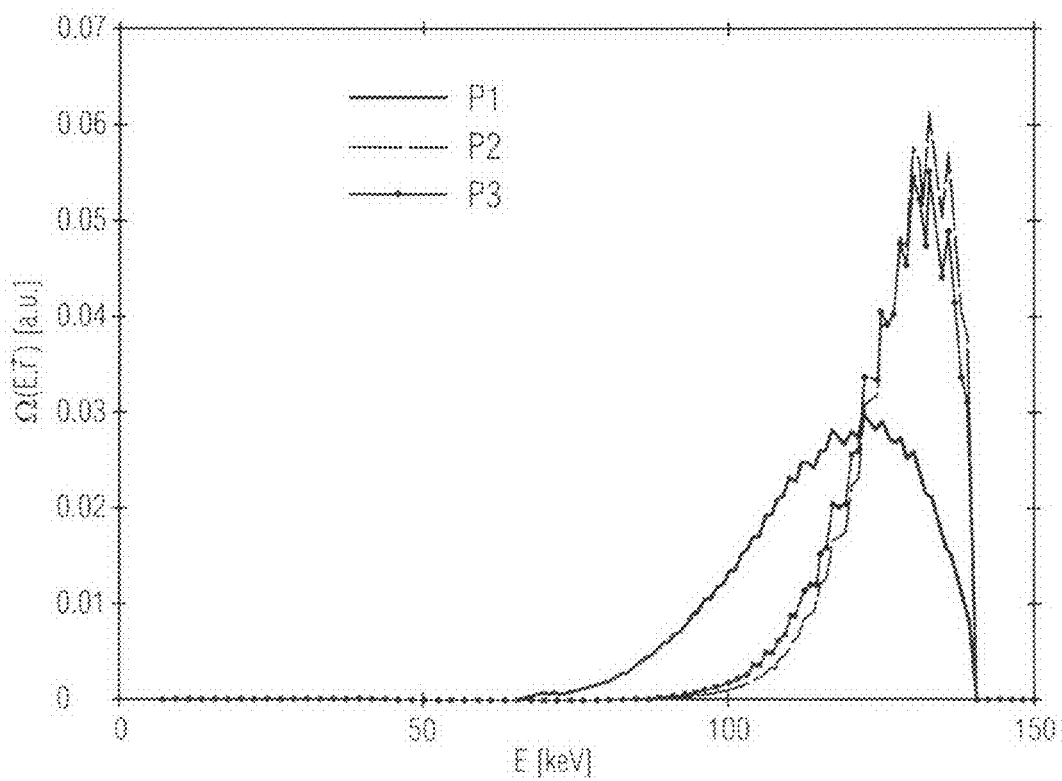
FIG. 14: Example local measurement-spectrum-dependent weighting functions Ω(E,$\vec{r}_0$) at the measurement points P1-P3 of FIG. 13 using the radiation detector combination with 140 kVp radiation applied over energy.

FIG. 14 shows three local measurement-spectrum-dependent weighting functions $\Omega_j(E,\vec{r})$, which have been calculated, by way of example, at the locations P1, P2 and P3 of a measurement field with a phantom 7 shown in FIG. 13. For this purpose the spectrum of a 140 kVp x-ray beam of a CT system was used as the basis. The effect of beam hardening can be detected in the course of the weighting functions at the locations P1, P2 and P3, which experience an ever greater displacement to the more intense spectrum the more central the measurement point selected.

Figure 15:
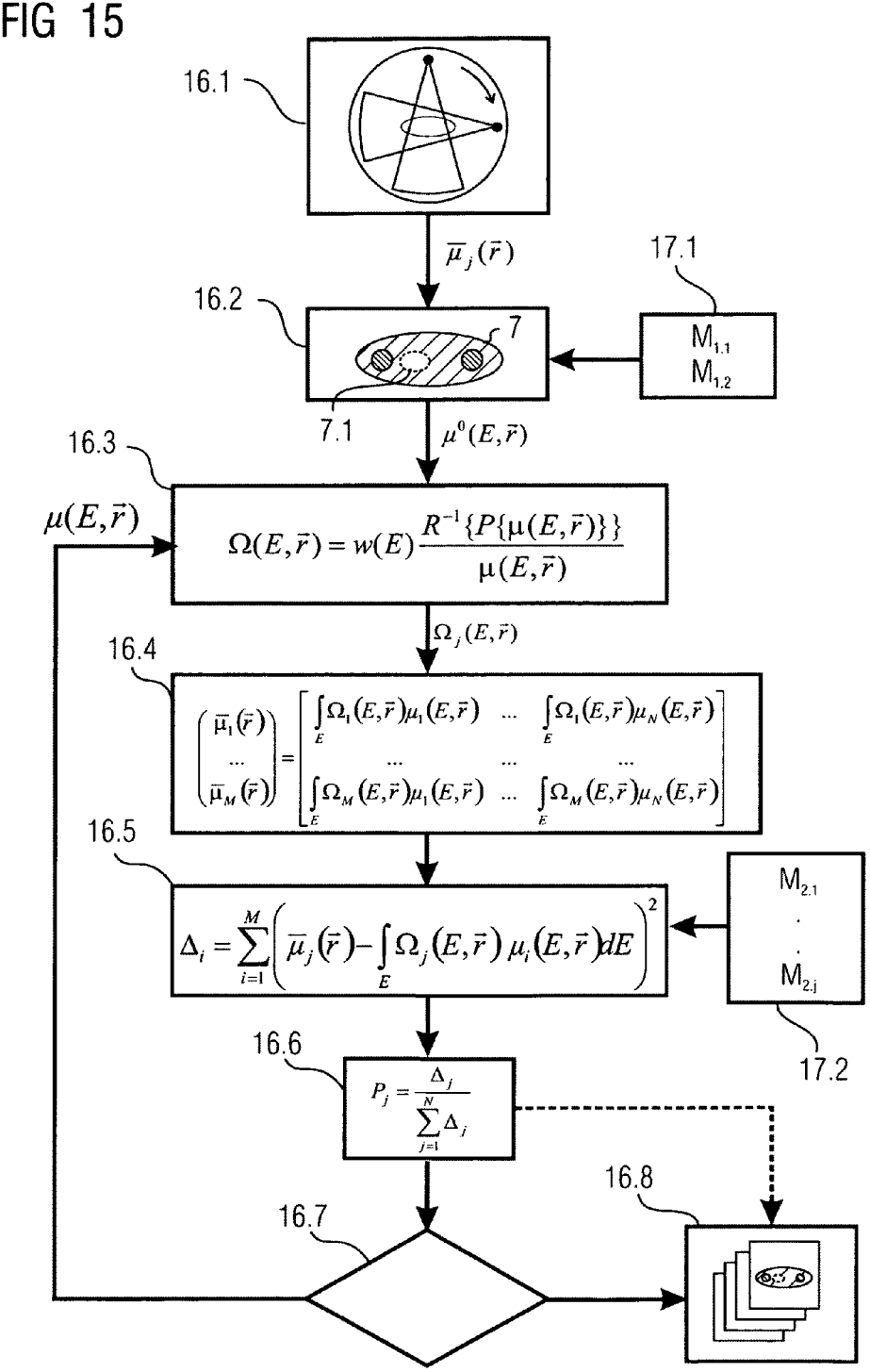
FIG. 15: Flowchart showing the inventive method with iteration.

A schematic illustration of this inventive process is shown, with an exemplary embodiment using iteration, in FIG. 15 with method steps 16.1 to 16.8 illustrated.

In the first method step 16.1 an examination object 7 is scanned using a CT system with reference to at least two different scanning spectra, and the local mean attenuation values $\bar{\mu}_j(\vec{r})$ are reconstructed. The index j here defines the different spectral weighting functions of the radiation detector combinations used. In step 16.2, on the basis of the calculated data records of the local mean attenuation values $\bar{\mu}_j(\vec{r})$, an initial approximate material distribution is determined in the examination object and possibly also in the measurement field—in this case, for example, an examination couch is also included in the measurement field—for which purpose only the reference materials $M_{1,x}$ defined in a first list 17.1 are used. In this case the first index 1 means that it contains materials from the first list, while the second index x counts through the number of listed materials. From this first material distribution it is now possible, with the help of scientific tables, for the local energy-dependent attenuation functions $\mu^{(0)}(E,\vec{r})$ to be determined. From this process, in step 16.3, the local measurement-spectrum-dependent weighting functions or values $\Omega_j(E,\vec{r})$, are calculated as per equation 11—or even as per equation 12.

On the basis of the local measurement-spectrum-dependent weighting functions $\Omega_j(E,\vec{r})$ thus determined and the measured and reconstructed local mean attenuation values $\bar{\mu}_j(\vec{r})$, a detailed calculation of local energy-dependent attenuation functions $\mu(E,\vec{r})$ can now be carried out in method step 16.4.

In the next method step 16.5, a comparison is carried out with reference materials $M_{2,x}$ from a second list 17.2, wherein the first index defines that it contains materials from the second list, whilst the second index x in turn counts through the number of listed materials. In this step deviations between the measured local mean attenuation values $\bar{\mu}_j(E,\vec{r})$ and the theoretical local mean attenuation values are calculated, $$\bar{\mu}_{theoretical}(\vec{r}) = \int_E \Omega_j(E, \vec{r})\mu(E, \vec{r})dE$$

with the latest determined local measurement-spectrum-dependent weighting functions $\Omega_j(E,\vec{r})$ and the local measurement-spectrum-dependent attenuation functions $\mu(E,\vec{r})$ being determined. By way of example, the equation $$\Delta_i = \sum_{i=1}^{M} \left( \bar{\mu}_j(\vec{r}) - \int_E \Omega_j(E, \vec{r})\mu_i(E, \vec{r})dE \right)^2$$

may be used for this purpose.

In step 16.6, probabilities $$P_j = \frac{\Delta_j}{\sum_{j=1}^{N} \Delta_j}$$

are calculated for each i-th reference material. The reference material which is given the greatest probability may be taken to be the most plausible at the observed location.

If iterative calculation is not carried out, the calculated data may now be displayed in step 16.8, wherein a tomographical display is mostly selected in which the different materials are shown with different colors. In addition, different concentrations or probabilities may be displayed with the help of color intensities.

If an iterative calculation takes place, it is possible to branch back to method step 16.3 from step 16.6 as a result of an iteration decision 16.7 if the previous result is not yet adequately converged. In this case better knowledge of the material distribution is now incorporated into the further calculation. If there is already sufficient convergence of iterations or if sufficient iteration steps have been carried out, then the iteration is interrupted and the process branches to the display as per step 16.8.

The user consequently has image data available which is no longer dependent upon the radiation used for the examination and which enables the examination object and its material distribution to be displayed irrespective of the measurement system used.

It should also be noted that reconstructed CT image data records mean the actual spectrally weighted and thus measurement-spectrum-dependent attenuation values $\mu$ that are measured by an x-ray spectrum, even though, in the display of these reconstructed CT image data records, so-called CT counts or CT values X in HU (=Hounsfield Units) are mostly shown in a gray scale. The conversion between CT value X and attenuation value $\mu$ standardized to water is carried out according to the equation $$X = \frac{\mu - \mu_{Water}}{\mu_{Water}} \cdot 1000.$$

In summary, therefore, in at least one embodiment of the invention it is proposed that an initial material distribution of an examination object is determined from CT data records determined from among at least two different spectral weightings with local energy-determined attenuation values, and local measurement-spectrum-dependent weighting functions are determined using this material distribution, enabling local measurement-spectrum-dependent attenuation functions to be calculated, wherein—with the help of local plausibility considerations—the distribution of local reference materials is determined from a list of reference materials over at least one specified region of interest in the examination object on the basis of the previously calculated local measurement-spectrum-dependent attenuation functions. This method may be combined with all above-mentioned features within the scope of the invention.

In particular, the aforementioned features of the invention may be used not only in the combination specified, but also in other combinations or in isolation, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for preparing reconstructed CT image data records from $N \geq 2$ projection data records, recorded with N different spectral weightings, defined as a product function of the energy-dependent weighting of a radiation spectrum used and a spectral sensitivity of a detector that is used, the method comprising:

CT scanning an examination object and generating N projection data records, each measured with different spectral weightings;

reconstructing N CT image data records, each with a large number of local image values, which reflect local mean attenuation values at a location of the examination object and of a measurement field depending on respective energy-dependent spectral weightings used for the CT scanning;

establishing a first list of reference materials with known mean attenuation values, which permit an initial approximate calculation of beam hardening in the examination object;

establishing a second list of reference materials with known mean attenuation values, which may be present in the examination object;

calculating an initial approximate distribution of reference materials in the examination object by comparing the previously calculated local mean attenuation values with the mean attenuation values from the first list of reference materials;

determining a distribution of local energy-dependent attenuation functions in the examination object on the basis of the last known distribution of reference materials and previously known material-specific energy-dependent attenuation functions;

calculating local measurement-spectrum-dependent weighting functions at the locations of the examination object on the basis of the last known material distribution in the examination object with the with the associated material-specific energy-dependent attenuation functions;

determining the distribution of reference materials from the second list of reference materials according to plausibility principles over at least one specified region of interest in the examination object on the basis of previously calculated local energy-dependent attenuation functions; and displaying the determined distribution of reference materials from the second list at least in the specified region of interest in the examination object.

2. The method as claimed in claim 1, wherein, for the determining according to plausibility principals, deviations between measured local mean attenuation coefficients and calculated local spectrally weighted attenuation coefficients are evaluated from the local measurement-spectrum-dependent attenuation functions and the local measurement-spectrum-dependent weighting functions of the reference materials from the second list.

3. The method as claimed in claim 2, wherein, in order to determine the deviations $\Delta_j$ the equation $$\Delta_j = \sum_{i=1}^{M} \left( \bar{\mu}_i(\vec{r}) - \int_E \Omega_i(E,\vec{r}) \mu_j(E,\vec{r}) dE \right)^2$$

is used, wherein j represents the index for the reference material, $$\left( \int_E \Omega_i(E,\vec{r}) \mu_j(E,\vec{r}) dE \right)$$

represents the calculated local spectrally weighted attenuation coefficients, wherein $\Omega_j(E,\vec{r})$ represents the determined local measurement-spectrum-dependent weighting functions at locations ($\vec{r}$), and $\mu_j(E,\vec{r})$ represents the measurement-spectrum-dependent attenuation functions, and ($\bar{\mu}_i(\vec{r})$) represents the measured local mean attenuation coefficients.

4. The method as claimed in claim 3, wherein plausibility for the occurrence of a j-th material at the observed location is equated with the probability $P_j$ and calculated using $$P_j = \frac{\Delta_j}{\sum_{j=1}^{N} \Delta_j}.$$

5. The method as claimed in claim 1, wherein, after the determining of the distribution of reference materials, the steps of determining a distribution of local energy-dependent attenuation functions, calculating local measurement-spectrum-dependent weighting functions, and determining the distribution of reference materials are performed iteratively until a predefined iteration condition is met.

6. The method as claimed in claim 5, wherein, in order to calculate the local measurement-spectrum-dependent weighting functions ($\Omega(E,\vec{r})$) at the locations ($\vec{r}$) of the examination object, the equation $$\Omega(E, \vec{r}) = w(E, \vec{r}) \frac{\overline{\mu}(\vec{r})}{\mu(E, \vec{r})}$$

is used in which:

$$\overline{\mu}(\vec{r}) = R^{-1}\{P\{\mu(E, \vec{r})\}\}$$

$$\text{and } w(E) = \frac{S(E)D(E)}{\int_E S(E')D(E')dE'},$$

wherein
w(E) is a spectral weighting function,
w(E,$\vec{r}$) is the spectral weighting function at the locations ($\vec{r}$),
$\overline{\mu}(\vec{r})$ is a measured mean attenuation values,
$\mu(E,\vec{r})$ is the energy-dependent attenuation and material-specific attenuation functions,
S(E) is a spectral weighting of a radiation spectrum,
D(E) is a detector sensitivity,
P is the forward projection operator in a reconstruction of a CT image data record, and
$R^{-1}$ is the radon transformation operator in a reconstruction of a CT image data record.

7. The method as claimed in claim 1, wherein a patient is used as the examination object.

8. The method as claimed in claim 1, wherein the first list of the reference materials contains a selection of two to four materials from the following list: water, tissue, bone, air and contrast medium.

9. The method as claimed in claim 1, wherein the second list of reference materials contains a selection of two to four materials from the following list: water, tissue, bone, air and contrast medium.

10. The method as claimed in claim 1, wherein the first list of reference materials contains the following materials:
healthy organ-specific tissue and malignant organ-specific tissue.

11. The method as claimed in claim 1, wherein the second list of reference materials consists of the following materials: healthy organ-specific tissue and malignant organ-specific tissue.

12. The method as claimed in claim 1, wherein the region of interest in the examination object is the entire scanned area of the patient.

13. The method as claimed in claim 1, wherein the region of interest in the examination object is an organ of the patient.

14. The method as claimed in claim 1, wherein the region of interest in the examination object is a segmented area of the patient.

15. The method as claimed in claim 1, wherein the region of interest in the examination object is a manually selected area of the patient.

16. The method as claimed in claim 1, wherein an inanimate object is used as the examination object.

17. The method as claimed in claim 16, wherein only the materials processed in the examination object are used in the first list and the second list of reference materials.

18. The method as claimed in claim 17, wherein the first list and the second list of reference materials are differentiated in that at least one the material sought in the object is used in the second list.

19. The method as claimed in claim 16, wherein the first list and the second list of reference materials are differentiated in that at least one the material sought in the object is used in the second list.

20. The method as claimed in claim 1, wherein different energy-dependent spectral weightings are achieved by the use of different radiation spectra.

21. The method as claimed in claim 1, wherein different energy-dependent spectral weightings are achieved by the use of different spectral detector sensitivities.

22. The method as claimed in claim 1, wherein the CT scan of the examination object is carried out over a large number of scanning angles arranged with equal distribution.

23. A method, comprising:
determining, by a processor associated with a CT system, an initial material distribution of an examination object from CT data records determined from among at least two different spectral weightings with local spectrally weighted and measurement-spectrum-dependent attenuation values;
determining, by the processor and using the determined initial material distribution, local measurement-spectrum-dependent weighting functions which enable local energy-dependent and measurement-spectrum-dependent attenuation functions to be calculated; and
determining, by the processor and using plausibility considerations, a distribution of reference materials from a list of reference materials over at least one specified region of interest in the examination object on the basis of previously calculated local energy-dependent and measurement-spectrum-dependent attenuation functions.

24. A CT system for scanning an examination object, comprising:
a control unit; and
the processor with a memory, the memory storing computer program code to execute the method steps of method claim 23 during operation.

25. A non-transitory computer readable medium including program segments for, when executed on a computer device, causing the computer device to implement the method of claim 1.

26. A non-transitory computer readable medium including program segments for, when executed on a computer device, causing the computer device to implement the method of claim 23.

27. A CT system for scanning an examination object, comprising:
- means for determining an initial material distribution of an examination object from CT data records determined from among at least two different spectral weightings with local spectrally weighted and measurement-spectrum-dependent attenuation values;
- means for determining, using the determined initial material distribution, local measurement-spectrum-dependent weighting functions which enable local energy-dependent and measurement-spectrum-dependent attenuation functions to be calculated; and
- means for determining, using plausibility considerations, a distribution of reference materials from a list of reference materials over at least one specified region of interest in the examination object on the basis of previously calculated local energy-dependent and measurement-spectrum-dependent attenuation functions.

* * * * *